(12) United States Patent
Monsé

(10) Patent No.: US 8,677,844 B2
(45) Date of Patent: Mar. 25, 2014

(54) INJECTION PORT FOR ANALYSIS APPLIANCES, DEVICE FOR ACTUATING AN INJECTION PORT, AND ANALYSIS APPLIANCE WITH AN INJECTION PORT

(75) Inventor: Christian Monsé, Bochum (DE)

(73) Assignee: Dimatec Analysentechnik GmbH, Essen (DE)

( * ) Notice: Subject to any disclaimer, the term of this patent is extended or adjusted under 35 U.S.C. 154(b) by 753 days.

(21) Appl. No.: 12/671,699

(22) PCT Filed: Aug. 1, 2008

(86) PCT No.: PCT/DE2008/001259
§ 371 (c)(1),
(2), (4) Date: Jan. 2, 2011

(87) PCT Pub. No.: WO2009/015656
PCT Pub. Date: Feb. 5, 2009

(65) Prior Publication Data
US 2011/0088458 A1    Apr. 21, 2011

(30) Foreign Application Priority Data
Aug. 2, 2007 (DE) .......................... 10 2007 036 612

(51) Int. Cl.
*G01N 1/00* (2006.01)

(52) U.S. Cl.
USPC ..................... 73/864.85; 73/61.56; 73/61.59

(58) Field of Classification Search
USPC ........ 73/61.55, 61.56, 61.59, 863.85, 863.86, 73/863.71, 863.73, 864.21, 864.22, 73/864.81, 864.85, 864.87; 96/105, 106; 422/568
See application file for complete search history.

(56) References Cited

U.S. PATENT DOCUMENTS

| | | | |
|---|---|---|---|
| 4,022,065 A | 5/1977 | Ramin | |
| 4,403,520 A | 9/1983 | Sisti | |
| 4,422,860 A | 12/1983 | Feinstein | |
| 4,896,545 A | 1/1990 | Averette | |
| 4,915,356 A | 4/1990 | Guild | |
| 4,954,149 A * | 9/1990 | Fullemann | ...................... 96/105 |
| 2002/0131902 A1 | 9/2002 | Levy | |
| 2004/0013572 A1* | 1/2004 | Moore et al. | ................... 422/99 |

FOREIGN PATENT DOCUMENTS

| | | |
|---|---|---|
| WO | 93/11696 A | 6/1993 |
| WO | 2005/013883 A | 2/2005 |
| WO | 20081/68663 A | 6/2008 |

* cited by examiner

*Primary Examiner* — Hezron E Williams
*Assistant Examiner* — Nathaniel Kolb
(74) *Attorney, Agent, or Firm* — Gudrun E. Huckett

(57) ABSTRACT

The invention relates to an injection port for analysis appliances, said injection port (10), when fitted correctly on an analysis appliance, forming an access line which leads to an analysis chamber of the analysis appliance and through which it is possible to guide the cannula of a sample injector containing a sample to be analysed, characterized in that the injection port comprises at least one elastic valve element (24) which can be opened and closed in a controlled manner and by means of which the access line to the analysis chamber can be sealed off both in the absence of a cannula and also when a cannula is guided through the injection port. The invention further relates to an analysis appliance provided with a corresponding injection port, and to a device for actuating the injection port.

25 Claims, 2 Drawing Sheets

INJECTION PORT FOR ANALYSIS APPLIANCES, DEVICE FOR ACTUATING AN INJECTION PORT, AND ANALYSIS APPLIANCE WITH AN INJECTION PORT

TECHNICAL FIELD OF THE INVENTION

The invention concerns an injection port for analysis appliances in which a sample to be analyzed is dispensed by means of a sample dispenser into an analysis chamber. The invention concerns also an arrangement for actuation of the injection port as well as an analysis appliance provided with a respective injection port.

BACKGROUND OF THE INVENTION

In case of analysis appliances of the kind in question a liquid sample to be analyzed is generally automatically sucked in by means of a sample dispenser from a vessel containing the sample to be analyzed by means of a cannula and, after appropriate new positioning of the sample dispenser, is injected into the analysis chamber, which is for example a reactor in which the sample is evaporated, and subsequently analyzed.

For various reasons it is desirable that the analysis chamber before, during, and after analysis is exposed only to a limited extent to ambient air. For example, it may be desirable that before the analysis ambient air cannot penetrate into the analysis chamber and possibly falsify the measurement. When the sample to be analyzed is evaporated in the analysis chamber, the gases that are produced thereby should be supplied as completely as possible to appropriate sensors and should not escape in an uncontrolled fashion into the environment. After the analysis, the analysis chamber can be flushed, for example, with an inert gas that also should not escape in an uncontrolled fashion into the environment. On the other hand, the cannula of the sample dispenser must be insertable into the analysis chamber so that an access to the analysis chamber is required for the cannula.

Up to now the aforementioned access to the analysis chamber is realized by means of a septum that is simply punctured by means of the cannula of the sample dispenser and that, at least when new, provides a sufficient sealing action for the analysis chamber with inserted cannula as well as after pulling out the cannula. Since however automatic sample dispensers in general operate very precisely, the punctuation of the septum occurs always at the same location which leads to a fast aging of the septum that therefore must be exchanged relatively frequently. In case of automatic analysis appliances that operate sequentially without supervision for many hours and theoretically can analyze thousands of samples without requiring a human intervention for maintenance, the exchange of the septum that up to now could only be done manually is a significant impairment of the efficiency and represents a significant cost factor.

SUMMARY OF THE INVENTION

The invention has the object to provide an injection port for analysis appliances as well as an analysis appliance provided with a respective injection port with which the desired closable access for a cannula of a sample dispenser can be realized without a septum and wherein the maintenance expenditure is significantly reduced. The invention has also the object to provide an arrangement for actuating the injection port according to the invention with which an especially safe and economic operation of the injection port can be ensured.

The object is solved by an injection port that has at least one elastic valve element that can be opened and closed in a controlled fashion and by means of which the access to the analysis chamber can be sealed when the cannula is missing as well as when the cannula extends through the injection port. The object is solved also by an arrangement for actuating an injection port, wherein the valve element is connected by means of a 3/2-way valve with a pressure source for loading the valve element with a pressurized fluid or gas, wherein between the pressure source and the 3/2-way valve a flow limiter and between the flow limiter and the 3/2-way valve a buffer tank for a pressurized fluid are provided. The object is solved also by an analysis appliance provided with an injection port that comprises at least one elastic valve element that can be opened and closed in a controlled fashion and by means of which the access to the analysis chamber can be sealed when the cannula is missing as well as when the cannula extends through the injection port. Advantageous embodiments and further developments are the subject matter of the respective dependent claims.

The invention has the great advantage that by means of an elastic valve element that can be opened and closed in a controlled fashion the access to the analysis chamber by the cannula can be sealed with the cannula missing as well as with inserted cannula. Upon insertion of the cannula, the valve element can be opened to such an extent that the cannula passes without contact through the injection port so that no wear is produced and the valve element has a very long service life.

Further details and advantages of the invention result from the following description of an embodiment in connection with the drawing.

DESCRIPTION OF PREFERRED EMBODIMENTS

Figure 1:
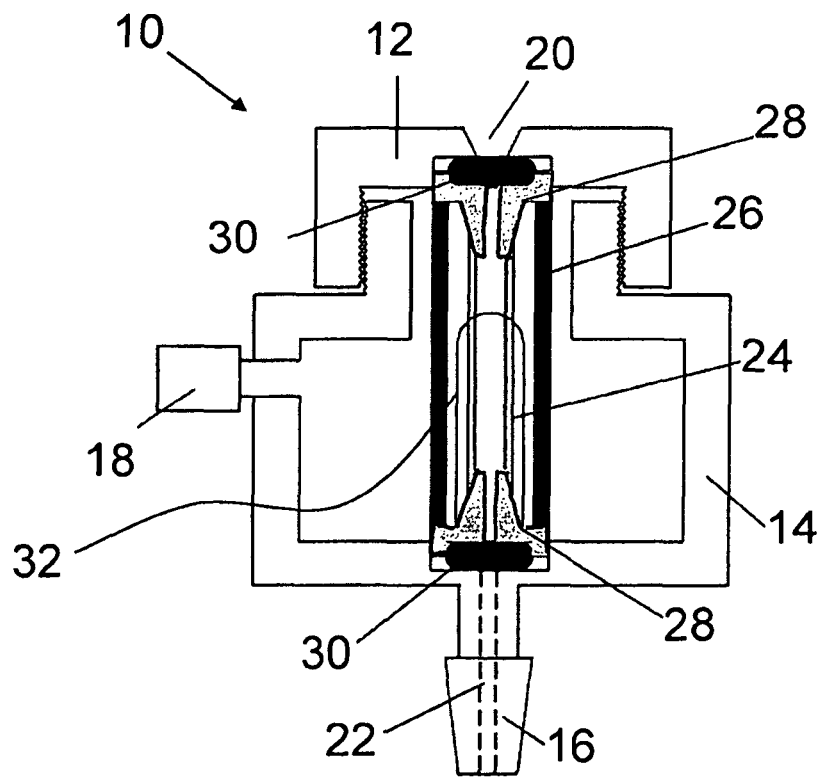
FIG. 1 shows in greatly simplified sectional side view an injection port according to the invention.
Figure 2:
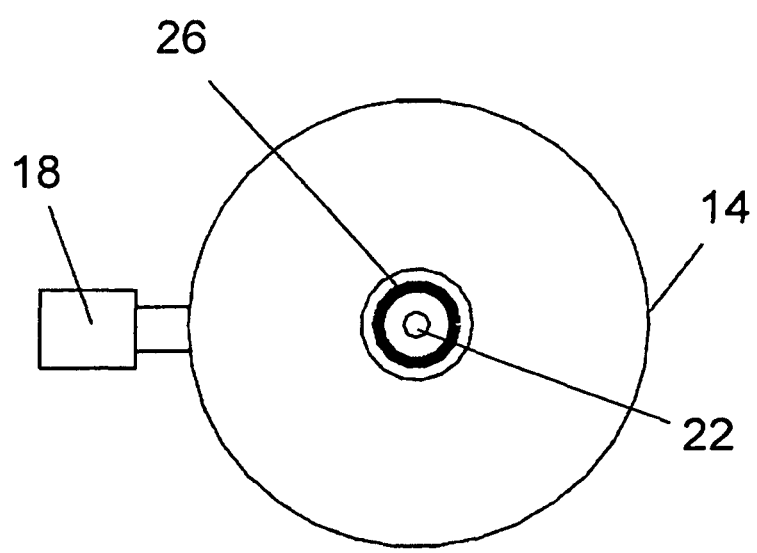
FIG. 2 shows the injection port according to FIG. 1 in a schematic plan view without O-ring and tube adapter.

In FIGS. 1 and 2 an injection port is shown that as a whole is referenced by 10 which in this embodiment is a two-part housing with a housing top part 12 and a housing bottom part 14. The housing top part 14 is provided with a connector in the form of a so-called luer cone 16 by means of which it can be connected to an analysis chamber of an analysis appliance, not shown in detail in this connection.

The housing bottom part 12 moreover has a connector 18 by means of which the injection port can be connected to a pressure source, in particular a compressed air source. The housing interior forms thus a chamber that can be pressurized and the valve element is a tube member through which a cannula of a sample dispenser can be passed, wherein the tube member is arranged in the chamber provided in the injection port that can be pressurized by means of a fluid or a gas such that the inner side of the tube member in the proper mounting state forms an access for a cannula of a sample dispenser, wherein by pressurizing the chamber when the cannula is missing the access to the analysis chamber can be closed by compression of the tube member and with inserted cannula the tube member can be tightly pressed against the cannula.

The operation of the injection port will be explained in connection with the description of FIG. 3 in more detail.

In the housing top part there is an inlet in the form of an opening 20 that conically tapers and in this way forms a centering aid for a cannula of a sample dispenser, not shown in detail in this connection and generally known in the art. The luer cone 16 has a through bore 22 that ends in an outlet for the cannula and that is positioned, when the housing top part 12 is placed on top, on an extension of the opening 20. When using the injection port, in this way a cannula of a sample dispenser can be guided via the insertion opening 20 through the injection port 10.

The housing top part 12 in this embodiment is screwed on in a seal-tight fashion onto the housing bottom part 14 for which purpose in this embodiment a section of the housing bottom part 14 is provided with an outer thread and a section of the housing top part 12 is provided with a complementary inner thread. Of course, also other fastening types between the housing parts are possible, for example, a flange connection. The illustrated screw-type connection of housing top part 12 and housing bottom part 14 has however the great advantage to be, on the one hand, inexpensive and realizable without further connecting parts, but, on the other hand, detachable easily so that by unscrewing the housing top part 12 the access to the parts of the injection port arranged inside the housing is possible.

In the housing between the inlet 20 and the luer cone 16 an elastic valve element, here in the form of a tube member 24, is disposed by means of a support tube 26, two tube adapters 28 that are provided at the two open ends of the support tube 26, and two O-rings 30 arranged between the two tube adapters 28 and the housing in such a way that a cannula of a sample dispenser that is guided from the opening 20 to the luer cone 16 can pass through the tube member 24 in its longitudinal direction. It should be mentioned in this context that FIG. 2 is a greatly simplified plan view in which the boundary lines of the top part 12, the upper O-ring 30 and the upper tube adapter 28 are not illustrated.

In the support tube 26 at least one recess that is indicated by the line 32 is provided in such a way that the tube member 24 is immediately exposed to the pressure conditions within the housing. The tube adapters 28 and the O-rings 30 seal together with the tube member 24 the housing interior relative to the exterior side of the housing so that, for example, a gas or a fluid that is guided through the connector 18 into the interior of the housing cannot escape via opening 20 or the bore 22. This configuration makes it possible that the tube member 24 by increasing the inner pressure in the housing can be compressed such that the access to the analysis chamber of an analysis appliance, not shown, which access is formed by the injection port, is closed such that neither ambient air can enter the analysis chamber nor the gases that are generated e.g. during an analysis can escape from the analysis chamber through the injection port. In this connection, the access can be closed for a cannula of a sample dispenser when removed as well as when extending through the injection port wherein in the latter case the tube is resting seal-tightly against the outer side of the cannula and the analysis chamber is connected of course through the cannula with the sample dispenser that is however generally itself designed such that through it no gases can escape in uncontrolled fashion from the analysis chamber.

The inner diameter of the tube member 24 is dimensioned advantageously such that it is somewhat greater than the outer diameter of a conventionally employed cannula. This makes it possible to pass the cannula without contact through the tube member when not loaded with pressure. In this way, no wear will be produced which significantly increases the service life of the tube member. The fact that in this embodiment the analysis chamber during insertion of the cannula is for a brief moment not closed gas-tightly by the injection port is not detrimental for most application situations. When however indeed a gas-tight closure is desired also for insertion of the cannula, the pressure in the housing interior can be reduced such that the tube member will rest against the cannula also during insertion but so that no high frictional forces between cannula and tube member are produced.

Figure 3:
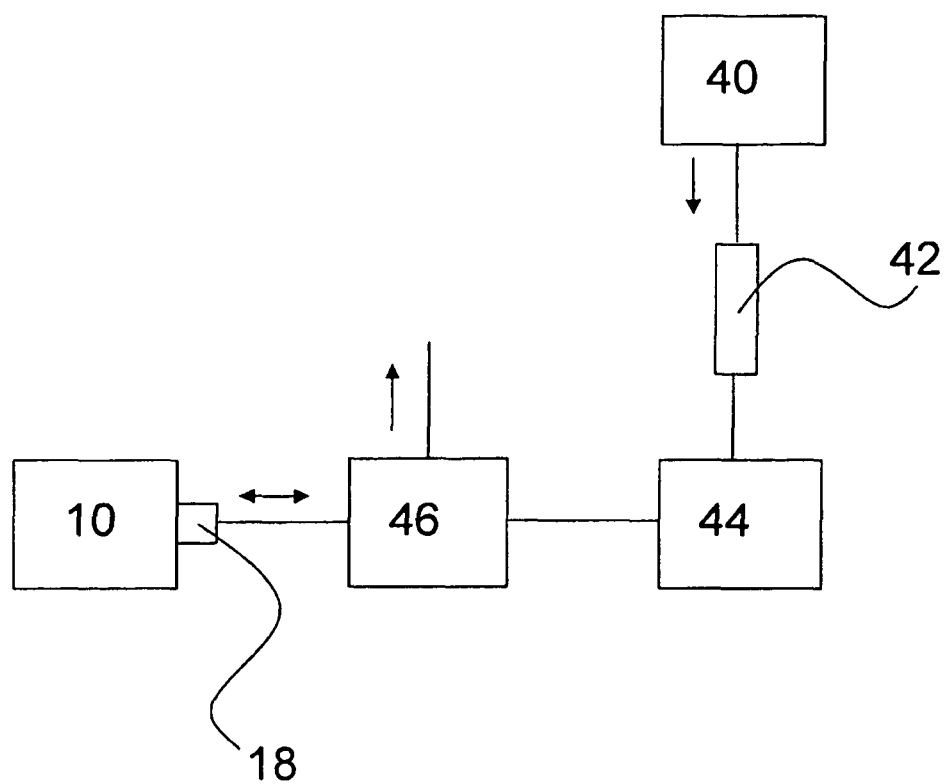
FIG. 3 shows schematically a device for controlled opening and closing of the valve element of the injection port according to the invention.

In FIG. 3, schematically a possible arrangement for actuation of the injection port 10, more precisely, of a valve element that is provided in the injection port is shown. The arrangement comprises a pressure source, here in the form of a compressed air tank 40, that is connected by means of a flow limiter, here in the form of a capillary tube 42, a buffer tank 44, and a 3/2-way valve 46 with the connector 18 of the injection port 10. Through the 3/2-way valve and an appropriate control, known in general, the elastic valve element that is provided in the injection port 10, i.e., the tube member illustrated in FIG. 1, can be loaded with or relieved from pressure in such a way that the valve element opens or closes. Since for closing the valve element no excessive pressure is required, the supply can be realized through the buffer tank 44 which enables, in conjunction with the flow limiter 42, to prevent excessive compressed air consumption of the arrangement, for example, in case of a defective elastic valve element in the injection port. The buffer tank, which has approximately a volume of 100 ml for dimensions of the injection port of conventional analysis appliances, is refilled through the flow limiter only with a greatly limited volume stream. In this way, it can be ensured that, for example, in case of a defective valve element in the injection port an air quantity of maximally only approximately 30 l per hour can escape.

In the context of the inventive principle numerous modifications and further developments are possible that concern, for example, the type of the employed valve element. For example, it is possible to employ instead of the illustrated tube member, that is compressed by external pressure in the desired way, an elastic double-walled element that is inflated or filled with a fluid such that its inner diameter is reduced in the desired way in order to close, with or without cannula, the access to an analysis chamber arranged downstream of the injection port. Also, it is possible to clamp the tube member, for example, in a U-shaped profiled section, instead of in the illustrated open support tube. For a person skilled in the art it is moreover apparent that the desired effect of opening and closing the elastic valve element also will be realized when the valve element is loaded with a fluid instead of with compressed air or with another gas. In most cases, however, an analysis appliance of the kind in question is provided also with a compressed air source so that the latter can be advantageously employed for actuation of the valve element of the injection port.

The invention claimed is:

1. An injection port for analysis appliances, wherein the injection port in a proper mounting state on an analysis appliance forms an access to an analysis chamber of the analysis appliance through which a cannula of a sample dispenser with a sample to be analyzed can be passed, the injection port comprising:
   at least one elastic valve element that opens and closes in a controlled fashion, wherein the at least one elastic valve element is configured to seal the access to the analysis chamber when the cannula is missing as well as when the cannula extends through the injection port;

wherein the at least one valve element is a double-walled tube element enabling passage of the cannula, wherein the tube element has an inner diameter that is reducible when filling in a gas or a fluid into an interior of the tube element.

2. The injection port according to claim 1, wherein the at least one elastic valve element is actuatable hydraulically or pneumatically.

3. An arrangement for actuating an injection port according to claim 2, comprising:
   a pressure source for loading the at least one elastic valve element with a pressurized fluid or gas;
   a 3/2-way valve that connects the at least one elastic valve element with the pressure source;
   a flow limiter arranged between the pressure source and the 3/2-way valve; and
   a buffer tank for a pressurized fluid arranged between the flow limiter and the 3/2-way valve.

4. The arrangement according to claim 3, wherein the pressure source is a compressed air source and the flow limiter is a capillary tube.

5. The injection port according to claim 1, comprising a housing with an inlet and an outlet for the cannula, wherein the at least one elastic valve element is arranged inside the housing.

6. The injection port according to claim 5, wherein the housing comprises a first part and a second part, wherein the first part of the housing is removable without the entire injection port being removed from the analysis appliance in order to access the at least one elastic valve element inside the housing.

7. The injection port according to claim 5, wherein the housing has a gas or fluid inlet for actuating the at least one elastic valve element by a gas or a fluid.

8. The injection port according to claim 5, wherein the at least one elastic valve element is arranged in the housing between the inlet and the outlet, wherein between the valve element and the inlet and between the valve element and the outlet an O-ring is arranged, respectively.

9. An injection port for analysis appliances, wherein the injection port in a proper mounting state on an analysis appliance forms an access to an analysis chamber of the analysis appliance through which a cannula of a sample dispenser with a sample to be analyzed can be passed, the injection port comprising:
   at least one elastic valve element that opens and closes in a controlled fashion, wherein the at least one elastic valve element is configured to seal the access to the analysis chamber when the cannula is missing as well as when the cannula extends through the injection port;
   a chamber that is configured to be pressurized by a fluid or a gas, wherein the at least one valve element is a tube member enabling passage of the cannula, wherein the tube member is arranged in the chamber such that an inner side of the tube member in a proper mounting state of the tube member forms an access for the cannula, wherein by pressurizing the chamber the access to the analysis chamber is closed by compression of the tube member when the cannula is missing or the tube member is tightly pressed against the cannula when the cannula is inserted into the tube member.

10. The injection port according to claim 9, wherein the tube member is clamped in an open support tube or in a U-shaped profiled section.

11. The injection port according to claim 9, wherein the at least one elastic valve element is actuatable hydraulically or pneumatically.

12. An arrangement for actuating an injection port according to claim 11, comprising:
   a pressure source for loading the at least one elastic valve element with a pressurized fluid or gas;
   a 3/2-way valve that connects the at least one elastic valve element with the pressure source;
   a flow limiter arranged between the pressure source and the 3/2-way valve; and
   a buffer tank for a pressurized fluid arranged between the flow limiter and the 3/2-way valve.

13. The arrangement according to claim 12, wherein the pressure source is a compressed air source and the flow limiter is a capillary tube.

14. The injection port according to claim 9, comprising a housing with an inlet and an outlet for the cannula, wherein the at least one elastic valve element is arranged inside the housing.

15. The injection port according to claim 14, wherein the housing comprises a first part and a second part, wherein the first part of the housing is removable without the entire injection port being removed from the analysis appliance in order to access the at least one elastic valve element inside the housing.

16. The injection port according to claim 14, wherein the housing has a gas or fluid inlet for actuating the at least one elastic valve element by a gas or a fluid.

17. The injection port according to claim 14, wherein the at least one elastic valve element is arranged in the housing between the inlet and the outlet, wherein between the valve element and the inlet and between the valve element and the outlet an O-ring is arranged, respectively.

18. An analysis appliance comprising:
   an analysis chamber into which a sample to be analyzed can be inserted by a sample dispenser with a cannula;
   an access to the analysis chamber provided for the cannula in the form of an injection port;
   wherein the injection port comprises at least one elastic valve element that opens and closes in a controlled fashion, wherein the at least one elastic valve element is configured to seal the access to the analysis chamber when the cannula is missing as well as when the cannula extends through the injection port;
   wherein the at least one valve element is a double-walled tube element enabling passage of the cannula, wherein the tube element has an inner diameter that is reducible when filling in a gas or a fluid into an interior of the tube element.

19. The analysis appliance according to claim 18, wherein the at least one elastic valve element is actuatable hydraulically or pneumatically.

20. The analysis appliance according to claim 18, wherein the injection port comprises a housing with an inlet and an outlet for the cannula, wherein the at least one elastic valve element is arranged inside the housing.

21. The analysis appliance according to claim 18, comprising an arrangement for actuation of the injection port, the arrangement comprising:
   a pressure source for loading the at least one elastic valve element with a pressurized fluid or gas;
   a 3/2-way valve that connects the at least one elastic valve element with the pressure source;
   a flow limiter arranged between the pressure source and the 3/2-way valve; and
   a buffer tank for a pressurized fluid arranged between the flow limiter and the 3/2-way valve.

22. An analysis appliance, comprising:
an analysis chamber into which a sample to be analyzed can be inserted by a sample dispenser with a cannula;
an access to the analysis chamber provided for the cannula in the form of an injection port;
wherein the injection port comprises at least one elastic valve element that opens and closes in a controlled fashion, wherein the at least one elastic valve element is configured to seal the access to the analysis chamber when the cannula is missing as well as when the cannula extends through the injection port;
wherein the injection port comprises a chamber that is configured to be pressurized by a fluid or a gas, wherein the at least one valve element is a tube member enabling passage of the cannula, wherein the tube member is arranged in the chamber such that an inner side of the tube member in a proper mounting state of the tube member forms an access for the cannula, wherein by pressurizing the chamber the access to the analysis chamber is closed by compression of the tube member when the cannula is missing or the tube member is tightly pressed against the cannula when the cannula is inserted into the tube member.

23. The analysis appliance according to claim 22, wherein the at least one elastic valve element is actuatable hydraulically or pneumatically.

24. The analysis appliance according to claim 22, wherein the injection port comprises a housing with an inlet and an outlet for the cannula, wherein the at least one elastic valve element is arranged inside the housing.

25. The analysis appliance according to claim 22, comprising an arrangement for actuation of the injection port, the arrangement comprising:
a pressure source for loading the at least one elastic valve element with a pressurized fluid or gas;
a 3/2-way valve that connects the at least one elastic valve element with the pressure source;
a flow limiter arranged between the pressure source and the 3/2-way valve; and
a buffer tank for a pressurized fluid arranged between the flow limiter and the 3/2-way valve.

* * * * *